United States Patent
Moritz et al.

(10) Patent No.: US 10,670,606 B2
(45) Date of Patent: *Jun. 2, 2020

(54) MASS SPECTROMETRY ANALYSIS OF MUTANT POLYPEPTIDES IN BIOLOGICAL SAMPLES

(71) Applicant: Cell Signaling Technology, Inc., Danvers, MA (US)

(72) Inventors: Albrecht Moritz, Salem, MA (US); John Edward Rush, II, Beverly, MA (US); Roberto Polakiewicz, Lexington, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,610

(22) Filed: Jul. 13, 2018

(65) Prior Publication Data

US 2019/0025322 A1    Jan. 24, 2019

Related U.S. Application Data

(60) Continuation of application No. 15/245,393, filed on Aug. 24, 2016, now Pat. No. 10,036,756, which is a division of application No. 12/931,445, filed on Feb. 1, 2011, now Pat. No. 9,453,845.

(60) Provisional application No. 61/300,212, filed on Feb. 1, 2010.

(51) Int. Cl.
| | |
|---|---|
| *G01N 33/68* | (2006.01) |
| *B01D 15/12* | (2006.01) |
| *B01D 15/32* | (2006.01) |
| *B01D 15/38* | (2006.01) |
| *B01D 15/42* | (2006.01) |
| *G01N 30/72* | (2006.01) |
| *H01J 49/00* | (2006.01) |

(52) U.S. Cl.
CPC ......... *G01N 33/6848* (2013.01); *B01D 15/12* (2013.01); *B01D 15/325* (2013.01); *B01D 15/3809* (2013.01); *B01D 15/3823* (2013.01); *B01D 15/422* (2013.01); *G01N 30/7233* (2013.01); *G01N 2560/00* (2013.01); *G01N 2570/00* (2013.01); *H01J 49/00* (2013.01)

(58) Field of Classification Search
CPC .. B01D 15/12; B01D 15/325; B01D 15/3809; B01D 15/3823; B01D 15/422; G01N 2560/00; G01N 2570/00; G01N 30/7233; G01N 33/6848; H01J 49/00

See application file for complete search history.

(56) References Cited

U.S. PATENT DOCUMENTS

| | | |
|---|---|---|
| 5,846,948 A | 12/1998 | Bruni |
| 6,441,140 B1 | 8/2002 | Comb et al. |
| 6,852,544 B2 | 2/2005 | Aebersold et al. |
| 6,982,318 B1 | 1/2006 | Comb et al. |
| 7,198,896 B2 | 4/2007 | Rush et al. |
| 7,259,022 B2 | 8/2007 | Comb et al. |
| 7,300,753 B2 | 11/2007 | Rush et al. |
| 7,332,613 B2 | 2/2008 | Gygi et al. |
| 7,344,714 B2 | 3/2008 | Comb et al. |
| 7,632,686 B2 | 12/2009 | Anderson |

(Continued)

FOREIGN PATENT DOCUMENTS

| | | |
|---|---|---|
| WO | 2004031730 A2 | 4/2004 |
| WO | 2005124341 A2 | 12/2005 |
| WO | 2009012420 A1 | 1/2009 |

OTHER PUBLICATIONS

Wada, "Detection and Characterization of Protein Mutations by Mass Spectrometry." The Protein Protocols Handbook. Third Edition, 2009, pp. 1081-1094.*

(Continued)

*Primary Examiner* — Marcela M Cordero Garcia
(74) *Attorney, Agent, or Firm* — DLA Piper LLP US (57) ABSTRACT

The invention relates to a method for determining the presence of at least one distinct polypeptide in a biological sample comprising contacting the biological sample with a hydrolyzing agent, wherein the hydrolyzing agent is capable of hydrolyzing the distinct polypeptide in a sequence-specific manner such that at least one distinct peptide having a predetermined peptide measured accurate mass would result if the at least one distinct polypeptide were present in the biological sample, to obtain a hydrolyzed sample; bringing the hydrolyzed sample in contact with a substrate comprising at least one immobilized binding partner, wherein the at least one immobilized binding partner is capable of specifically binding the distinct peptide; removing the hydrolyzed sample from the substrate in a manner such that the distinct peptide would remain bound to the immobilized binding partner; contacting the substrate with an elution solution, wherein the distinct peptide would dissociate from the immobilized binding partner into the elution solution; subjecting a portion of the elution solution to liquid chromatography to segregate a plurality of molecules in the portion of the elution solution to obtain sorted molecules; determining the measured accurate mass of at least one sorted molecule present in the elution solution; and determining the presence of the at least one distinct polypeptide in the biological sample when a measured accurate mass of at least one molecule is substantially equal to the predetermined peptide measured accurate mass.

20 Claims, 2 Drawing Sheets

(56) References Cited

U.S. PATENT DOCUMENTS

| | | | |
|---|---|---|---|
| 7,794,947 B2* | 9/2010 | Aebersold | C12Q 1/37 435/7.1 |
| 9,453,845 B2* | 9/2016 | Moritz | G01N 33/6848 |
| 10,036,756 B2* | 7/2018 | Moritz | B01D 15/3823 |
| 2003/0068652 A1 | 4/2003 | Comb et al. | |
| 2005/0092910 A1 | 5/2005 | Geromanos et al. | |
| 2006/0148093 A1 | 7/2006 | Gygi et al. | |
| 2006/0154318 A1 | 7/2006 | Anderson | |
| 2007/0026461 A1 | 2/2007 | Comb et al. | |
| 2007/0275483 A1 | 11/2007 | Liotta | |
| 2009/0011459 A1 | 1/2009 | Kiga | |
| 2009/0042993 A1 | 2/2009 | Puglielli | |
| 2009/0286283 A1 | 11/2009 | Lee | |

OTHER PUBLICATIONS

Peng et al., "A proteomics approach to understanding protein ubiquitination." Nature Biotechnology, 2003. vol. 21, No. 3, pp. 921-926.*

Stemmann et al., "Dual Inhibition of Sister Chromatid Separation at Metaphase." Cell, Dec. 14, 2001, vol. 107, pp. 715-726.*

Merrell et al., "Analysis of Low-Abundance, Low-Molecular-Weight Serum Proteins Using Mass Spectrometry." J Biomolecular Techniques, 2004, pp. 238-248.*

Gravatt et al., "The biological impact of mass-spectrometry-based proteomics." Nature, 2007, vol. 450, pp. 991-1000.*

Wang et al., "Mutant proteins as cancer-specific biomarkers." PNAS, 2011, pp. 2444-2449.*

Anderson et al., "Quantitative Mass Spectrometric Multiple Reaction Monitoring Assays for Major Plasma Proteins." Molecular and Cellular Proteomics, 2006. vol. 5, pp. 573-588.*

Malehom et al., "Detection of Cystic Fibrosis Mutations by Peptide Mass Signature Genotyping." Clinical Chemistry, 2003, vol. 49, No. 8, pp. 1318-1330.*

Anderson et al., "Mass Spectrometric Quantitaion of Peptides and Proteins Using Stable Isotope Standards and Capture by Anti-Peptide Antibodies (SISCAPA)." Journal of Proteome Research, published on the web Feb. 6, 2004, vol. 3, No. 2, pp. 235-244.*

Gstaiger et al., "Applying mass spectrometry-based proteomics to genetics, genomics and network biology." Nature Reviews. Genetics, 2009. vol. 10, pp. 617-711.*

Huang et al., "Affinity Purification of Proteins Using Ligands Derived from Peptide Libraries." 1995. Biotechnology and Bioengineering, vol. 47, pp. 288-297.*

Brock et al., "Detection and identification of arginine modifications on methylglyoxal-modified ribonuclease by mass spectrometric analysis." J. Mass Spectrom. 2007, vol. 42, pp. 89-100.*

Kim et al., "Substrate and Functional Diversity of Lysine Acetylation Revealed by a Proteomics Survey." Molecular Cell. 2006, vol. 23, pp. 607-618.*

Yu et al., "Mutation-Specific Antibodies for the Detection of EGFR Mutations in Non-Small-Cell-Lung Cancer", Clin Cancer Res, 15(9):3023-3028 (2009).

* cited by examiner

MASS SPECTROMETRY ANALYSIS OF MUTANT POLYPEPTIDES IN BIOLOGICAL SAMPLES

CROSS-REFERENCE TO RELATED APPLICATIONS

This application is a continuation of U.S. Ser. No. 12/931,445, filed Feb. 1, 2011, which claims priority to U.S. provisional patent application Ser. No. 61/300,212 filed Feb. 1, 2010, the entire contents of both applications, which are incorporated herein by reference.

FIELD OF THE INVENTION

The invention encompasses methods and apparatuses for the rapid proteomic analysis of complex biological samples. Specifically, the invention provides for rapid fractionation of the biological samples and subsequent simultaneous analysis of the fractionate for the presence or absence of a large number of polypeptides in general and mutant peptides in particular.

BACKGROUND OF THE INVENTION

Personalized medicine is the application of genomic and molecular data to better target the delivery of health care to specific patients, facilitate the discovery and clinical testing of new products, and help determine a person's predisposition to a particular disease or condition.

On a technical level, personalized medicine depends on the identification and detection of proteins, genes and genetic variation ("biomarkers") that play a role in a given disease. Rodland, Clin Biochem. 2004 July; 37(7):579-83. The presence or absence of certain biomarkers is then correlated with the incidence of a particular disease or disease predisposition. However, currently available methods for biomarker analysis are associated with long waiting periods, high cost and numerous technical hurdles.

Massspectrometry (MS) is an important method for the characterization of proteins in biological samples. MS involves ionizing chemical compounds to generate charged molecules or molecule fragments and measurement of their mass or mass-to-charge ratios. In a typical MS procedure, a sample is loaded onto the MS instrument, and undergoes vaporization. The components of the sample are ionized by one of a variety of methods (e.g., by impacting them with an electron beam), which results in the formation of positively charged particles (ions). The positive ions are then accelerated by a magnetic field. The computation of the mass-to-charge ratio of the particles is based on the details of motion of the ions as they transit through electromagnetic fields, and detection of the ions.

The two primary methods for MS ionization are electrospray ionization (ESI) and matrix-assisted laser desorption/ionization (MALDI). Generally, however, proteins must be enzymatically digested into smaller peptides using a protease prior to ionization and analysis. The resulting peptides are introduced into the mass spectrometer and identified by peptide mass fingerprinting or tandem mass spectrometry. Identification of certain peptides allows the technician to infer the existence of particular proteins in an original sample.

Proteins of interest to biological researchers are usually part of a very complex mixture of other proteins and molecules that co-exist in the biological medium (e.g., serum, blood, urine, tissue sample, mucous, saliva, stool, etc.). This presents two significant problems. First, the two ionization techniques used for large molecules (i.e., ESI and MALDI) only work well when the mixture contains roughly equal amounts of constituents. However, different proteins tend to be present in widely differing amounts in biological samples. If such a mixture is ionized using ESI or MALDI, the more abundant species have a tendency to "drown" or suppress signals from less abundant ones. The second problem is that the mass spectrum from a complex mixture is very difficult to interpret because of the overwhelming number of mixture proteins. This complexity is exacerbated by the usually necessary enzymatic digestion of a protein prior to MS analysis. As such, biological media must generally be laboriously pre-processed before MS analysis can be performed.

Two pre-processing methods are usually used to fractionate proteins, or their peptide products from an enzymatic digestion, prior to MS analysis: Two-dimensional ("2-D") gel electrophoresis and high performance liquid chromatography ("HPLC").

Two-dimensional ("2-D") gel electrophoresis separates a mixture of proteins by two properties in two dimensions on 2D gels. See e.g., Kossowska et al., Postepy Hig Med Dosw (Online). 2009 Nov. 12; 63:549-63; Ma et al., Electrophoresis. 2009 August; 30(15):2591-9. 2-D electrophoresis begins with 1-D electrophoresis but then separates the molecules by a second property in direction 90 degrees from the first. The result is that the molecules are spread out across a 2-D gel. Because it is unlikely that two molecules will be similar in two distinct properties, molecules are more effectively separated in 2-D electrophoresis than in 1-D electrophoresis. However, 2-D electrophoresis is a time (30 minutes to 12 hours per sample) and labor intensive process requiring complex as well as very expensive equipment and highly trained and experienced technicians.

Fractionation of peptides after enzymatic digestion into multiple fractions by HPLC (e.g. by SCX) prior to MS analysis is also commonly used. Yet all these fractions must be analyzed to separately, greatly increasing time and effort spent on a single sample.

Apart from these fractionation methods prior to MS analysis, MS itself is often combined with HPLC which is generally referred to as "LC-MS." LC-MS is a powerful technique used for many applications which has very high sensitivity and specificity.

The "bottom-up" approach to proteomics involves protease digestion and denaturation followed by LC-MS with peptide mass fingerprinting; or LC-MS/MS (or "two-stage" or "tandem MS") to derive the sequence of individual peptides. See e.g., Shi et al., Anal Chem. 2009 Nov. 19; Grimsrud et al., Plant Physiol. 2009 Nov. 18; Kesic et al., Retrovirology. 2009 Nov. 17; 6:105; Kilpatrick et al., Anal Chem. 2009 Oct. 15; 81(20):8610-6. Wu et al., Anal Biochem. 2009 Nov. 3; Hartwig et al., Arch Physiol Biochem. 2009 Nov. 4; Caron et al., Mol Cell Proteomics. 2007 July; 6(7):1115-22. Epub 2007 Mar. 20.

A tandem mass spectrometer is one capable of multiple rounds of mass spectrometry, usually separated by some form of molecule fragmentation. Tandem mass spectrometry allow for a variety of experimental sequences. Normally, a tandem MS has at least two mass spectrometers in series connected by a chamber that can break a molecule into pieces. A sample peptide is sorted and weighed in the first mass spectrometer (MS1), broken into pieces in the collision cell, and a peptide piece or pieces again sorted and weighed in the second mass spectrometer (MS2). Many commercial mass spectrometers are designed to expedite the execution of sequences as single reaction monitoring (SRM), multiple reaction monitoring (MRM), and precursor ion scan. In SRM, the MS1 allows only a single mass through and MS2 monitors for a single user defined fragment ion. MRM allows for multiple user defined fragment ions. Unfortunately, SRM and MRM require complex and expensive instrumentation and computer equipment.

LC-MS/MS is most commonly used for proteomic analysis of complex samples. Samples of complex biological fluids like human serum may be run through an LC-MS/MS system and result in over 1000 proteins being identified. However, to achieve such results, samples are generally first separated on an SDS-PAGE gel or strong cation exchange ("SCX") HPLC.

Recently, it has been reported that the MRM assay can be coupled with a strategy to enrich certain peptides: Stable Isotope Standards with Capture by Anti-Peptide Antibodies ("SISCAPA"). In the method, anti-peptide antibodies immobilized on 100 nanoliter nanoaffinity columns are used to enrich specific peptides along with spiked stable-isotope-labeled internal standards of the same sequence. Upon elution from the anti-peptide antibody supports, SRM/MRM tandem MS is used to quantify the peptides (natural and labeled). See Whiteaker et al., Mol Cell Proteomics. 2009 Oct. 20; Ahn et al., J Proteome Res. 2009 September; 8(9):4216-24; Kuhn et al., Clin Chem. 2009 June; 55(6): 108-17. Epub 2009 Apr. 16; Anderson et al., Mol Cell Proteomics. 2009 May; 8(5):995-1005. Epub 2009 Feb. 4; Anderson et al., Mol Cell Proteomics. 2006 April; 5(4):573-88. Epub 2005 Dec. 6; Anderson et al., J Proteome Res. 2004 March-April; 3(2):235-44; US Pub. Nos. 20060154318, 20070231909, 20080217254.

The inventor has developed a simplified method that can rapidly fractionate and analyze a biological sample for the presence or absence of a particular protein or peptide analytes by measured accurate mass alone (i.e., using only MI) without the need to for complex and expensive tandem MS or MS2 procedures and equipment.

SUMMARY OF THE INVENTION

One aspect of the invention relates to a method for determining the presence of at least one distinct polypeptide in a biological sample comprising contacting the biological sample with a hydrolyzing agent, wherein the hydrolyzing agent is capable of hydrolyzing the distinct polypeptide in a sequence-specific manner such that at least one distinct peptide having a predetermined peptide measured accurate mass would result if the at least one distinct polypeptide were present in the biological sample, to obtain a hydrolyzed sample; bringing the hydrolyzed sample in contact with a substrate comprising at least one immobilized binding partner, wherein the at least one immobilized binding partner is capable of specifically binding the distinct peptide; removing the hydrolyzed sample from the substrate in a manner such that the distinct peptide would remain bound to the immobilized binding partner, contacting the substrate with an elution solution, wherein the distinct peptide would dissociate from the immobilized binding partner into the elution solution, to obtain an elution solution comprising a plurality of molecules; determining the measured accurate mass of at least one sorted molecule present in the elution solution; and determining the presence of the at least one distinct polypeptide in the biological sample when a measured accurate mass of at least one molecule is substantially equal to the predetermined peptide measured accurate mass.

In a preferred embodiment, the portion of the elution solution further comprises at least one standard peptide, wherein the at least one standard peptide has the same amino acid sequence as the at least one distinct peptide but a different measured accurate mass (by way of incorporation of certain isotopes, for example). In this embodiment, the at least one standard peptide and the at least one distinct peptide co-segregate during liquid chromatography, confirming the chemical identity of the at least one distinct peptide in addition to identification by accurate mass.

In another aspect, the invention provides a method for determining the presence of at least one distinct polypeptide in a biological sample. The method comprises the contacting the biological sample with a hydrolyzing agent, wherein the hydrolyzing agent is capable of hydrolyzing the distinct polypeptide in a sequence-specific manner such that at least one distinct peptide having a predetermined peptide measured accurate mass would result if the at least one distinct polypeptide were present in the biological sample, to obtain a hydrolyzed sample; bringing the hydrolyzed sample in contact with a substrate comprising at least one immobilized binding partner, wherein the at least one immobilized binding partner is capable of specifically binding the distinct peptide; removing the hydrolyzed sample from the substrate in a manner such that the distinct peptide would remain bound to the immobilized binding partner, contacting the substrate with an elution solution, wherein the distinct peptide would dissociate from the immobilized binding partner into the elution solution, to obtain an elution solution comprising a plurality of molecules; segregating the plurality of molecules by liquid chromatography to obtain sorted molecules; determining the measured accurate mass of at least one sorted molecule present in the elution solution; and Determining the presence of the at least one distinct polypeptide in the biological sample when a measured accurate mass of at least one sorted molecule is substantially equal to the predetermined peptide measured accurate mass.

In one embodiment of various aspects of the invention, at least one standard peptide is added to the plurality of molecules, wherein the at least one standard peptide has substantially the same amino acid sequence as the at least one distinct peptide but a different measured accurate mass. In some embodiments, the standard peptide comprises an isotope such as $^{15}N$, $^{13}C$, $^{18}O$, or $^{2}H$. In some embodiments, the at least one standard peptide and the at least one distinct peptide co-segregate during liquid chromatography.

In another embodiment, at least two reference peptides are added to the plurality of molecules, wherein the at least two reference peptides have known a known liquid chromatography elution order.

In another embodiment, the presence of the at least one distinct polypeptide is confirmed by the co-segregation of the at least one standard peptide and the at least one sorted molecule and by the difference in measured accurate mass between the at least one standard peptide and the at least one sorted molecule.

In various embodiments of the invention, the liquid chromatography is HPLC, is reverse phase HPLC, or is reverse phase C18 HPLC.

In further embodiments, the plurality of molecules are segregated during liquid chromatography according to hydrophobicity, according to charge, or according to retention time. In some embodiment, the at least one standard peptide and the at least one distinct peptide have a substantially identical retention time.

In another embodiment the at least one distinct polypeptide is a mutant polypeptide relative to a wild type polypeptide. In further embodiments, the difference between the mutant polypeptide and wild type polypeptide is the addition, deletion and/or substitution of about 1 to about 10 amino acid residues, or is the addition, deletion and/or substitution of a post-translational modification on at least one amino acid residue. In some embodiments, the post-translational modification is selected from the group consisting of phosphorylation, acetylation, ubiquitination, and glycosylation. In some embodiments, the at least one distinct peptide comprises a mutant signature.

In yet another embodiment, the biological sample is derived from saliva, mucous, tears, blood, serum, lymph fluids, buccal cells, circulating tumor cells, mucosal cells, biopsy tissue, cerebrospinal fluid, semen, feces, plasma, urine, a suspension of cells, or a suspension of cells and viruses. In further embodiments, the biological sample comprises between about 5,000 to about 20,000 different polypeptides, or between about 7,500 to about 15,000 different polypeptides, or up to about 100,000 different polypeptides and isoforms thereof. In some embodiment of the various methods of the invention, the biological sample is depleted of a protein selected from the group consisting of albumin, IgG, IgA, transferrin, haptoglobin, and anti-trypsin; or combinations thereof, prior to step (a).

In further embodiments, the hydrolyzing agent is an enzyme, a chemical (e.g., cyanogen bromide, BNPS-Skatole or formic acid). In further embodiments, the hydrolyzing agent is selected from the group consisting of trypsin, Lysine-C endopeptidase (LysC), arginine-C endopeptidase (ArgC), Asp-N, glutamic acid, endopeptidase (GluC), chymotrypsin and combinations thereof.

In yet further embodiments the substrate comprises a gel matrix or polymer beads. The gel matrix and/or the polymer beads may comprise a linking moiety to couple the immobilized binding partner.

In another embodiment the at least one immobilized binding partner comprises an antibody or peptide binding fragment thereof.

In another embodiment the at least one immobilized binding partner comprises a protein that specifically binds to the distinct peptide, or comprises an antibody or antibody fragment that binds a mutant signature peptide, or comprises an antibody or antibody fragment that binds a wild type peptide.

In another embodiment, the at least one immobilized binding partner is 1 to about 500 or 1 to at least 500 immobilized binding partners, wherein each immobilized binding partner specifically binds to a different distinct peptide.

In another embodiment, the determining measure accurate mass includes the step of ionization of the at least one molecule by Atmospheric Pressure Chemical Ionisation (APCI), Chemical Ionisation (CI), Electron Impact (EI), Electrospray Ionisation (ESI), Fast Atom Bombardment (FAB), Field Desorption/Field Ionisation (FD/FI), Matrix Assisted Laser Desorption Ionisation (MALDI), or Thermospray Ionisation. In some embodiments, the ionization is Electrospray Ionisation (ESI).

In further embodiments, the determining the measured accurate mass is performed using an instrument with a mass accuracy of 5 ppm or less, or an instrument with a mass accuracy of 1 ppm or less.

Another aspect of the invention relates to apparatuses capable of performing the aforementioned methods. In some embodiments, the apparatus for carrying out the method comprises a mass spectrometer or comprises an LC-MS.

A further aspect of the invention relates to kits comprising reagents for performing the aforementioned methods.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which.

DETAILED DESCRIPTION OF THE PREFERRED EMBODIMENTS

Previously, biological mixtures having more than 2-3 proteins typically require the additional use of tandem MS ("MS/MS") and/or MS2 based protein identification to achieve sufficient specificity of identification. See Clauser et al., Anal. Chem., 1999, 71 (14), pp 2871-2882. However, the methods of the invention do not require the use of MS2-peptide fragmentation to arrive at a definitive result with respect to the presence or absence of a plurality of mutant polypeptides in a biological sample. By not requiring MS2 analysis (e.g., SRM or MRM techniques), the methods disclosed herein can be carried out in any lab set up with basic affinity chromatography and MS1 capability. Moreover, the methods of the invention are readily adaptable for mass implementation without the need for specialized equipment requiring highly skilled and experienced technicians. For example, the disclosed techniques are readily adaptable to existing LC-MS systems (e.g., Thermo Fischer's Exactive® System) or miniaturization utilizing microfluidic technology.

Prior to describing various embodiments of the current invention, the following definitions are provided:

As used herein the term "peptide" or "polypeptide" refers to a polymer formed from the linking, in a defined order, of preferably, α-amino acids. The link between one amino acid residue and the next is called an amide bond or a peptide bond. Proteins are polypeptide molecules (or having multiple polypeptide subunits). The distinction is that peptides are preferably short and polypeptides/proteins are preferably longer amino acid chains. The term "protein" is intended to also encompass derivatized molecules (e.g., post-translational modified polypeptides) such as glycoproteins and lipoproteins as well as lower molecular weight polypeptides. The invention aims to identify the presence of certain proteins or polypeptides in a biological sample by identifying the presence of a peptide portion of the protein or polypeptide, by way of the peptide's predicted measured accurate mass.

The term "standard peptide" as used herein, refers to a peptide that is: 1) recognized as equivalent to a peptide of interest in the digest, e.g., the mutant signature peptide, by an appropriate immobilized binding partner(s); 2) co-elutes through LC with a peptide of interest in the digest, e.g., the mutant signature peptide; and 3) differs from the peptide of interest in a manner that can be distinguished by a mass spectrometer. Preferably, the standard peptide has the same amino acid sequence as the mutant signature peptide but is synthesized utilizing elemental isotopes. Preferably, those isotopes are $^{15}$N, $^{13}$C, $^{18}$O or $^{2}$H. One or more standard peptides may be added to the biological sample before or after treatment with hydrolyzing agent such that it co-elutes with the peptide of interest into the elution solution. Alternatively, the standard can be added directly to the elution solution. Exemplary standard peptides are described in U.S. Pub. No. 20060154318.

In a preferred embodiment of the invention, at least one standard peptide is added to either the biological sample, hydrolyzed sample and/or elution solution such that the standard peptides enter into the LC-MS device at the same time as the peptides being analyzed. In this embodiment, the standard peptides will preferably have the same amino acid sequence as the peptide of interest as well as a different yet known, mass. Most preferably, the standard peptide and the peptide of interest will co-elute through LC and therefore, have substantially the same retention time. If the technician determines the presence of two co-LC-eluting peptides different only with respect to a mass they can confirm the presence of the peptide of interest and therefore, the polypeptide of interest in the biological sample.

The term "wild type polypeptide" refers to the phenotype of the typical form of a polypeptide or protein as it most often occurs in nature and/or which is associated with normal polypeptide or protein physiologic function.

Generally, a "mutant polypeptide" differs from the wild type polypeptide with respect to amino acid sequence variation and/or post-translational modification (i.e., the "mutant signature"). The segment of amino acid(s) of a mutant polypeptide that contains such variability is also referred to herein as a "mutant signature peptide."

Mutant polypeptides may be the result of normal inter-individual genetic variability and/or may be associated with aberrant polypeptide or protein physiologic function.

A mutant polypeptide may be associated with the addition, deletion and/or substitution of one or more preferably, about 1 to about 10, preferably about 1 to about 5, or more preferably about 1 to about 3, or about 1 to about 2 amino acid residues relative to their wild type counterpart.

By "post-translational modification" is meant a change to a polypeptide that occurs after that polypeptide is translated from mRNA by a ribosome. Pos-translational modifications include but are not limited to the addition or deletion of biochemical functional groups such as acetate, phosphate, various lipids and carbohydrates. Non-limiting examples of specific post-translational modifications include: Acylation; deacetylation; methylation; alkylation; amidation; biotinylation; formylation; gamma-carboxylation; glutamylation; glycosylation; glycation; glycylation; hydroxylation; iodination; isoprenylation; lipoylation; prenylation; GPI anchor formation; myristoylation; farnesylation; geranylgeranylation; diphthamide; ADP-ribosylation; flavin attachment; oxidation; palmitoylation; pegylation; phosphatidylinositol attachment; phosphopantetheinylation; phosphorylation—usually of a serine, tyrosine, threonine or histidine residue; polysialylation; pyroglutamate formation; arginylation, sulfation; ubiquitination, sumoylation; and selenoylation.

As used herein, the term "biological sample" refers to a readily obtainable mixture of a plurality of polypeptides present in varying concentrations. Preferred biological samples have up to about 100,000 different polypeptides (including isoforms thereof). Preferably the biological samples include about 5,000 to about 20,000 different polypeptides. More preferably, biological samples have about 7,500 to about 15,000 different polypeptides. Most preferably, biological samples have about 10,000 different polypeptides. Generally, such samples are environmental, industrial, veterinary or medical in origin. The preferred biological samples include but are not limited to saliva, mucous, tears, blood, serum, lymph/interstitial fluids, buccal cells, mucosal cells, biopsy tissue, cerebrospinal fluid, semen, feces, plasma, urine, a suspension of cells, or a suspension of cells and viruses. The most preferred biological samples are mammalian, more preferably human biopsy, serum, and urine.

Where the biological sample is blood, serum or lymph/interstitial fluid, the invention envisages an optional step of depleting the biological sample of common and disproportionally over-represented background proteins not suspected of being associated with mutant polypeptides. Such proteins include but are not limited to albumin, IgG, IgA, transferrin, haptoglobin, and anti-trypsin; or combinations thereof. The skilled artisan will recognized that such a step is carried out by basic affinity chromatography techniques. As used herein the term "depleted" or "depleting" means markedly lessening the concentration of a particular species in a solution, e.g., by more than or about 50%; more than or about 60%; more than or about 65%; more than or about 70%; more than or about 75%; more than or about 80%; more than or about 85%; more than or about 90%; more than or about 92%; more than or about 95%; more than or about 97%; more than or about 98%; more than or about 99%.

As used herein, the term "hydrolyzing agent" refers to any one or combination of a large number of different enzymes, including but not limited to trypsin, Lysine-C endopeptidase (LysC), arginine-C endopeptidase (ArgC), Asp-N, glutamic acid endopeptidase (GluC) and chymotrypsin, V8 protease and the like, as well as chemicals, such as but not limited to cyanogen bromide, BNPS-Skatole and formic acid. In the subject invention one or a combination of hydrolyzing agents cleave peptide bonds in a protein or polypeptide, in a sequence-specific manner, generating a predictable collection of shorter peptides (a "digest"). A portion of the biological samples are contacted with hydrolyzing agent(s) to form a digest of the biological sample. Given that the amino acid sequences of certain polypeptides and proteins in biological samples are often known and that the hydrolyzing agent(s) cuts in a sequence-specific manner, the shorter peptides in the digest are generally of a predicable amino acid sequence. Preferably, the treatment of a polypeptide with a hydrolyzing agent results in the polypeptides being split into peptides about 5 to about 50 acids in length. If the polypeptide in a biological sample is a mutant polypeptide, at least one of the resulting peptides in the digest will be a mutant signature peptide.

The term "hydrolyzed sample" (also referred to as a "digest") refers to a solution of peptides that is the result of a portion of the biological sample having been exposed to one or more hydrolyzing agents.

The term "mass spectrometer" means a device capable of detecting specific molecular species and measuring their accurate masses. The term is meant to include any molecular detector into which a polypeptide or peptide may be eluted for detection and/or characterization. In the preferred MS procedure, a sample, e.g., the elution solution, is loaded onto the MS instrument, and undergoes vaporization. The components of the sample are ionized by one of a variety of methods (e.g., by impacting them with an electron beam), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. The preferred error rate of a mass spectrometer of the invention is 3 ppm or less, and most preferably 1 ppm or less. The present invention is surprisingly advantageous as it allows for the identification polypeptides in general and mutant polypeptides in particular in biological samples by way of accurate mass alone without the need to use tandem MS or. MS2. This advantage arises in part due to enrichment of the peptides by the immobilized binding partners in the elution solution relative to the hydrolyzed sample or a biological sample which thereby reduces the overall complexity of the elution solution relative to the hydrolyzed sample or biological sample.

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement with about 5 ppm or preferably less uncertainty is sufficient to uniquely determine the elemental composition of molecules, e.g., enriched peptides, in the elution solution.

As used herein the term, "predetermined peptide accurate mass" refers to the experimentally determined or calculated accurate mass of a peptide with a known amino acid sequence (along with any associated post-translational modifications). The accurate mass of any such specific amino acid sequence may be readily calculated by one of skill in the art.

The term "substrate" includes any solid support or phase upon which a binding partner may be immobilized. Preferred supports are those well known in the art of affinity chromatography for example but not limited to polymeric and optionally magnetic beads, polystyrene, sepharose or agarose gel matrices, or nitrocellulose membranes or the like. Preferably, the substrate contains a linkage moiety for coupling to the immobilized binding partner. Such coupling might be through an avidin/biotin linkage or linkage through protein A or protein G agarose, for example.

The term "immobilized binding partner" refers to any of a large number of different molecules or aggregates which are linked to the substrate.

In the invention, a binding partner functions by binding to a polypeptide or peptide in order to enrich it prior to determining its accurate mass. Preferably, mutant signature peptides are bound and enriched. Proteins, polypeptides, peptides, nucleic acids (oligonucleotides and polynucleotides), antibodies, ligands, polysaccharides, microorganisms, receptors, antibiotics, and test compounds (particularly those produced by combinatorial chemistry) may each be a binding partner. The preferred binding partner is an antibody or peptide-binding fragment thereof which specifically yet reversibly binds peptides and/or mutant signature peptides.

It should be understood that the substrate can contain many different immobilized binding partners having a different binding specificity for a different polypeptide, peptide or mutant signature peptide. As such, immobilized binding partners might be derived from monoclonal sources or polyclonal sera. Preferably, the substrate has 2 to about 500 or more; or at least 500 immobilized binding partners each specifically binding to a different distinct peptide. This allows the technician to simultaneously process and analyze the biological sample for the presence of a large number of polypeptides in a manner not feasible with multiplex PCR and immunohistochemical assays, and with far more accuracy than ELISA techniques and immunohistochemical assays. See also U.S. Pat. Nos. 6,441,140; 6,982,318; 7,198,896; 7,259,022; 7,300,753; 7,344,714; U.S. Ser. No. 11/484,485.

In one embodiment, the collection of immobilized binding partners on a substrate specifically recognizes one or more mutant signature peptides but does not recognize or cross react with wild type peptides.

In another embodiment, the collection of immobilized binding partners on a substrate binds to both mutant signature peptides and wild type peptides, e.g., by binding an epitope adjacent to or independent of the mutant signature.

The term "antibody" may be any of the classes of immunoglobulin molecules of any species, or any molecules derived therefrom, (e.g., ScFv) or any other specific binding partners constructed by variation of a conserved molecular scaffold so as to specifically bind a polypeptide peptide fragment. The term "anti-peptide antibody" may be any type of antibody that binds a specific peptide, mutant signature peptide, or other fragment for the purposes of enrichment from a sample or processed sample.

The term "specifically binds" is commonly used and well understood by the person of ordinary skill in the art with respect to the binding partners. An antibody that specifically binds to a target may also be referred to as a target-specific antibody. For example, a mutant-specific antibody specifically binds to the mutant polypeptide and does not bind to the wild-type polypeptide. Non-limiting mutant-specific antibodies include an EGFR E746-A750del-specific antibody that does not bind got wild-type EGFR (e.g., product 2085 sold by Cell Signaling Technology, Inc., Danvers, Mass.) and an EGFR L858R-specific antibody that does not bind to wild-type EGFR (e.g., product 3197 sold by Cell Signaling Technology, Inc). Additional non-limiting mutant-specific antibodies include antibodies such as the Phospho-c-Abl (Tyr245)-specific antibody sold by Cell Signaling Technology, Inc. (product 2868) that specifically binds to c-Abl when phosphorylated at Tyr245 but does not bind to wild-type c-Abl (i.e., does not bind non-phosphorylated at Tyr245) and the Acetyl-Histone H4 (Lys12)-specific antibody sold by Cell Signaling Technology, Inc. (product 2591) that specifically binds to Histone H4 only when it is acetylated on Lys12 but does not bind wild-type Histone H4 (i.e., does not bind Histone H4 when H4 is not acetylated on Lys12).

The term "elution solution" refers to a solution that when brought into contact with the immobilized binding partner and substrate, results in the dissociation of the polypeptide or peptide and preferably the mutant signature peptide from the immobilized binding partner into the elution solutions. Determining the salt, pH and ionic conditions necessary for such functionality is well within the ordinary skill in the art.

Preferably, the elution solution is far less complex than the biological sample of the hydrolyzed sample. It is preferably substantially enriched for peptides which were bound to the immobilized binding partners relative to the polypeptides and peptides of the hydrolyzed sample. Preferably, the elution solution has about 1 to about 5000, more preferably about 10 to about 1009 different peptides. Most preferably, the elution solution is enriched for mutant signature peptides. The substantial reduction in the complexity of the elution solution relative to the hydrolyzed sample and biological sample allows for efficient sorting of the enriched peptides in the elution solution during the LC-MS.

The term "vaporizing a portion of the elution solution" means that a portion of the elution solution is preferably transferred to a mass spectrometer for vaporization and ionization.

The term "ionizing" refers to atmospheric pressure chemical ionization (APCI), chemical ionization (CI), electron impact (EI), electrospray ionization (ESI), fast atom bombardment (FAB), field desorption/field ionization (FD/FI), matrix assisted laser desorption ionization (MALDI), and thermospray ionization. The preferred method of ionization is ESI.

As used herein, "ionized molecule" refers to molecules in the elution solution that have become charged and are ready to move into the electric fields that will direct them into the mass analyzer of a mass spectrometer. Preferably, the ionized molecules include ionized polypeptides, peptides and/or mutant signature peptides present in the elution solution. Most preferably, the ionized molecules are mutant signature peptides.

"Chromatography" is a chemical separation technique that involves passing a mixture dissolved in a "mobile phase" through a stationary phase, which separates the analyte to be measured from other molecules in the mixture based on differential partitioning between the mobile and stationary phases.

"Liquid chromatography" or "LC" as used herein is a separation technique in which the mobile phase is a liquid. Liquid chromatography can be carried out either in a column or a plane. Preferably, the LC methods and equipment of the invention are coupled with a mass spectrometer.

Preferably, liquid chromatography uses relatively high pressure is referred to as high performance liquid chromatography ("HPLC"). HPLC is preferably used herein to separate, identify, and quantify compounds based on characteristics including but not limited to their idiosyncratic polarities and interactions with the column's stationary phase. Preferably, HPLC utilizes different types of stationary phase (typically, hydrophobic saturated carbon chains), a pump that moves the mobile phase(s) and analyte, e.g., peptide, through the column, and a detector that provides a characteristic retention time for the analyte. The HPLC preferably also provides other characteristic information (e.g., UV/Vis spectroscopic data for analyte). Peptide retention time varies depending on the strength of its interactions with the stationary phase, the ratio/composition of solvent(s) used, and the flow rate of the mobile phase.

In one embodiment, the HPLC involves reverse phase HPLC ("RP HPLC"). In RP HPLC, compounds are preferably separated based on their hydrophobic character. Preferably, peptides are be separated by running a linear gradient of an organic solvent. The preferred RP HPLC method utilizes a C18 column.

With respect to the analysis of the peptides herein, a run-to-run retention time accuracy (e.g. +/−2 minutes in a 45-minute gradient) is achievable with current generic liquid chromatography pumps.

Liquid chromatography-mass spectrometry ("LC-MS") is a technique that combines the physical separation capabilities of liquid chromatography (or HPLC) with the mass analysis capabilities of mass spectrometry.

A portion of the elution solution may be directly transferred to a mass spectrometer. Alternatively, a portion of the elution solution is subject to further manipulation e.g., to concentrate, to sort, or to order the peptides and/or polypeptides contained therein.

In the most preferred embodiment, a portion of the elution solution is analyzed using an LC-MS device. Preferably the LC device separates and orders the peptides (e.g., by retention time) present in the elution solution prior to the MS1 measurement of their accurate mass. In one embodiment, the retention times of the peptides present in the elution solution are matched with the measured accurate mass of the peptides. In another embodiment, the relative position of peptide elution is additionally aligned with a set of peptides the LC elution order and/or time of which is known (i.e., "reference peptides"). Mechanisms for directing solutions from liquid chromatography to mass spectrometers may be found for example in U.S. Pub. No. 20080217254.

In a preferred embodiment, the accurate mass of a molecule in the elution solution, e.g., a peptide combined with the LC co-elution of standard peptides of the same amino acid sequence but with a different accurate mass resulting from the incorporation of certain elemental isotopes. Preferably, the co-elution, e.g. on a mass spectrometer-coupled C18 column serves as confirmation of chemical identity and makes the identification of the peptide in the elution solution sample unambiguous.

The invention relates to methods and apparatuses which allow a technician to rapidly fractionate and analyze a complex biological sample for the presence or absence of a particular polypeptide by through affinity chromatography, liquid chromatography and MS1 mass spectrometry.

Future improvements in accuracy of mass measurement may*make chromatographic retention time of peptides unnecessary as a secondary characteristic. In that case, direct injection onto a mass spectrometer after enrichment by LAP, without prior LC-separation, may become a viable option.

One aspect of the invention involves a method for determining the presence or absence of a plurality of polypeptides in a biological sample such as biopsy, blood or serum. In a preferred embodiment of this aspect of the invention, the polypeptides in the biological sample are digested with a sequence-specific hydrolyzing agent such as the proteases GluC and/or trypsin. The resulting peptides of interest in the digest are then enriched by immunoaffinity purification using a variety of substrate-immobilized antibodies that recognize the peptides of interest. The affinity purified peptides of interest are then separated and ordered using LC. Subsequently, their accurate mass is determined by MS. The combination of a peptide's measured accurate mass and its position in the order of peptides sorted by LC (preferably determined by retention time), allows the technician to determine the identity of the peptide and determine whether it corresponds to the peptide of interest. Once the technician determines the presence of a particular peptide, they can extrapolate the presence of the polypeptide giving rise to that peptide in the biological sample.

In a preferred embodiment of this aspect of the invention, at least one standard peptide is added to either the biological sample, hydrolyzed sample and/or elution solution such that the standard peptides enter into the LC-MS device at the same time as the peptides being analyzed. In this embodiment, the standard peptides will preferably have the same amino acid sequence as the peptide of interest as well as a known mass different from the peptide of interest, e.g, by way of incorporation of certain isotopes. Most preferably, the standard peptide and the peptide of interest will co-elute during LC and therefore, have substantially the same retention time. If the technician determines the presence of two co-LC-eluting peptides different only with respect to a mass they can confirm the presence of the peptide of interest and therefore, the polypeptide of interest in the biological sample.

Certain diseases result from the presence or over-expression of mutant polypeptides. For example, Huntington's and Machado-Joseph disease are fatal inherited diseases caused by abnormal repeats of a small segment in a person's DNA resulting in the body producing malfunctioning proteins that cause the diseases. Further examples of such disease are Epidermolysis bullosa, sickle-cell disease, and SOD1 mediated ALS.

Additionally, an oncogene is a gene that, when mutated or expressed at high levels, can turn a normal cell into a tumor cell. A proto-oncogene is a normal gene that can become an oncogene due to mutations or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor-inducing agent, an oncogene. Examples of proto-oncogenes include RAS, WNT, MYC, ERK, and TRK, epidermal growth factor receptor (EGFR), platelet-derived growth factor receptor (PDGFR), and vascular endothelial growth factor receptor (VEGFR), HER2/neu, Src-family, Syk-ZAP-70 family, and BTK family of tyrosine kinases, the Abl gene in CML—Philadelphia chromosome, c-Sis and Raf kinase. In one non-limiting example, the proto-oncogene EGFR can give rise to several oncogenic mutants, and different mutants may be associated with different cancers. For example, many types of EGFR mutations have been reported, but the most common non-small cell lung cancer (NSCLC)-associated EGFR mutations are the 15-bp nucleotide in-frame deletion in exon 19 (E746-A750del) and the point mutation replacing leucine with arginine at codon 858 in exon 21 (L858R) (Pao, W., et al., Proc Natl Acad Sci USA, 2004. 101(36): p. 13306-11; Riely, G. J., et al., Clin Cancer Res, 2006. 12(24): p. 7232-41; and Kosaka, T., et al., Cancer Res, 2004. 64(24): p. 8919-23). These two mutations represent 85-90% of EGFR mutations in NSCLC patients. Importantly, patients with these mutations have been shown to respond well to EGFR inhibitors including Gefitinib and Erlotinib (Riely, G. J., et al., Clin Cancer Res, 2006. 12(24): p. 7232-41; Inoue, A., et al., J Clin Oncol, 2006. 24(21): p. 3340-6; Marchetti, A., et al., J Clin Oncol, 2005. 23(4): p. 857-65; and Mitsudomi, T., et al., J Clin Oncol, 2005. 23(11): p. 2513-20). Therefore detection of these mutations is an important method to improve treatment of lung cancer patients.

A tumor suppressor gene, or antioncogene, is a gene that protects a cell from one step on the path to cancer. When this gene is mutated to cause a loss or reduction in its function, the cell can progress to cancer, usually in combination with other genetic changes. Non-limiting examples of tumor suppressor genes are p53 tumor-suppressor protein encoded by the TP53 gene, PTEN, APC and CD95.

Accordingly, another aspect of the invention is a method of determining whether a patient is predisposed to or has a disease associated with the presence of a mutant polypeptide. Such mutant polypeptides may result from mutations in any of the above-listed genes including oncogenes, proto-oncogenes and tumor suppressor genes. In the preferred embodiment of this aspect of the invention, the technician can determine whether a patient is predisposed to or has a disease associated with the presence of a mutant polypeptide, if that mutant polypeptide is present in a biological sample obtained from the patient. Preferably, the patient's biological sample is simultaneously assayed for the presence of a plurality of mutant polypeptides according to the methods disclosed herein.

Another aspect of the invention relates to a method of determining whether a particular therapeutic regime or agent is effective in reducing the levels of a mutant polypeptide in a patient. In the preferred embodiment of this aspect of the invention, the method is used to determine the efficacy of a drug which is being provided to a patient having a particular disease, by determining whether the levels of mutant polypeptide associated with the disease are reduced in the biological sample. The preferred therapeutic agents of this embodiment are small molecules, polypeptides or nucleic acids, e.g., antisense nucleic acids, siRNA/miRNA constructs, etc. used to knockdown the expression of genes associated with the production of mutant polypeptides or directly cause the degradation of mutant polypeptides.

Another aspect of the invention relates to methods of screening drug candidates for potential use as therapeutic agents for disease associated with mutant polypeptides. In the preferred embodiment, a candidate drugs are given to a test animal. Preferably, the test animal has a disease associated with a mutant polypeptide. Biological samples from the animal are preferably assayed using the methods disclosed herein to determine if administration of the drug candidate has resulted in an increase or decrease in the level of the mutant polypeptide in the biological sample. Preferably, the test animal's biological sample is simultaneously assayed for the presence of a plurality of mutant polypeptides according to the methods disclosed herein.

A further aspect of the invention relates to methods of determining whether a particular test agent can give rise to a disease associated with the presence of one or more mutant polypeptides. In the preferred embodiment of this aspect of the invention, a normal or genetically sensitized animal (e.g., one containing a single copy of a loss of function mutation in a tumor suppressor gene) is provided with a test agent. Biological samples from the animal are preferably assayed using the methods disclosed herein to determine if administration of the test agent has resulted in an increase in the level of a mutant polypeptide in the biological sample. Preferably, the animal's biological sample is simultaneously assayed for the presence of a plurality of mutant polypeptides according to the methods disclosed herein.

Another aspect of the invention relates using the methods disclosed herein to determine whether a patient is predisposed to or has a disease associated with a mutant polypeptide. One embodiment of this aspect of the invention comprises: obtaining a biological sample from a patient suspected of being predisposed to or having the disease; contacting the biological sample with a hydrolyzing agent, wherein the hydrolyzing agent is capable of hydrolyzing the mutant polypeptide in a sequence-specific manner such that at least one mutant signature peptide having a predetermined mutant signature peptide measured accurate mass would result if the at least one mutant polypeptide were present in the biological sample, to obtain a hydrolyzed sample; bringing the hydrolyzed sample in contact with a substrate comprising at least one immobilized binding partner, wherein the at least one immobilized binding partner is capable of specifically binding the mutant signature peptide; removing the hydrolyzed sample from the substrate in a manner such that the mutant signature peptide would remain bound to the immobilized binding partner; contacting the substrate with an elution solution, wherein the mutant peptide would dissociate from the immobilized binding partner into the elution solution; determining the measured accurate mass of at least one molecule in the elution solution; and determining that the patient is predisposed to or has the disease when a measured accurate mass of the at least one molecule is substantially equal to the predetermined mutant signature peptide measured accurate mass.

A further aspect of the invention relates to using the methods disclosed herein to determine whether a therapeutic agent is effective in treating a patient having a disease associated with a mutant polypeptide. In a preferred embodiment of this aspect of the invention, the method comprises obtaining at least one control biological sample from the patient prior to administration of the therapeutic agent; obtaining at least one test biological sample from the patient after administration of the therapeutic agent; contacting the control biological sample with a hydrolyzing agent, wherein the hydrolyzing agent is capable of hydrolyzing the mutant polypeptide in a sequence-specific manner such that at least one mutant signature peptide having a predetermined mutant signature peptide measured accurate mass would result if the at least one mutant polypeptide were present in the control biological sample, to obtain a control hydrolyzed sample; contacting the test biological sample with the hydrolyzing agent, to obtain a test hydrolyzed sample; bringing the control hydrolyzed sample in contact with a control substrate comprising at least one immobilized binding partner, wherein the at least one immobilized binding partner is capable of specifically binding the mutant signature peptide; bringing the test hydrolyzed sample in contact with a test substrate comprising the immobilized binding partner; removing the control hydrolyzed sample from the control substrate in a manner such that the mutant signature peptide would remain bound to the immobilized binding partner; removing the test hydrolyzed sample from the test substrate in a manner such that the mutant signature peptide would remain bound to the immobilized binding partner; contacting the control substrate with a control elution solution, wherein the mutant peptide would dissociate from the immobilized binding partner into the control elution solution; contacting the test substrate with a test elution solution, wherein the mutant peptide would dissociate from the immobilized binding partner into the test elution solution; determining the measured accurate mass of at least one molecule in the control elution solution; determining the measured accurate mass of at least one molecule in the test elution solution; determining the presence of the mutant polypeptide in the control biological sample when a measured accurate mass of at least one molecule in the control elution solution is substantially equal to the predetermined mutant signature peptide measured accurate mass; determining the presence of the mutant polypeptide in the test biological sample by when a measured accurate mass of at least one molecule in the test elution solution is substantially equal to the predetermined mutant signature peptide measured accurate mass; determining the efficacy of the therapeutic agent when the mutant polypeptide is present in the control biological sample in a greater amount than in the test biological sample.

Yet a further aspect of the invention relates to the use of the methods disclosed herein to determine whether a test agent can result in a disease in a test subject associated with mutant polypeptide. The test subject may be for example an animal or human. In a preferred embodiment of this aspect of the invention, the method comprises obtaining at least one control biological sample from the test subject prior to administration of the agent; obtaining at least one test biological sample from the test subject after administration of the agent; contacting the control biological sample with a hydrolyzing agent, wherein the hydrolyzing agent is capable of hydrolyzing the mutant polypeptide in a sequence-specific manner such that at least one mutant signature peptide having a predetermined mutant signature peptide measured accurate mass would result if the at least one mutant polypeptide were present in the control biological sample, to obtain a control hydrolyzed sample; contacting the test biological sample with the hydrolyzing agent, to obtain a test hydrolyzed sample; bringing the control hydrolyzed sample in contact with a control substrate comprising at least one immobilized binding partner, wherein the at least one immobilized binding partner is capable of specifically binding the mutant signature peptide; bringing the test hydrolyzed sample in contact with a test substrate comprising the immobilized binding partner; removing the control hydrolyzed sample from the control substrate in a manner such that the mutant signature peptide would remain bound to the immobilized binding partner; removing the test hydrolyzed sample from the test substrate in a manner such that the mutant signature peptide would remain bound to the immobilized binding partner; contacting the control substrate with a control elution solution, wherein the mutant peptide would dissociate from the immobilized binding partner into the control elution solution; contacting the test substrate with a test elution solution, wherein the mutant peptide would dissociate from the immobilized binding partner into the test elution solution; determining the measured accurate mass of at least one molecule in the control elution solution; determining the measured accurate mass of at least one molecule in the test elution solution; determining the presence of the mutant polypeptide in the control biological sample when a measured accurate mass of at least one molecule in the control elution solution is substantially equal to the predetermined mutant signature peptide measured accurate mass; determining the presence of the mutant polypeptide in the test biological sample when a measured accurate mass of at least one molecule in the test elution solution is substantially equal to the predetermined mutant signature peptide measured accurate mass; determining that the test agent can result in a disease associated with a mutant polypeptide when the mutant polypeptide is present in the test biological sample but not in the control biological sample.

In embodiments of this aspect of the invention involving human test subjects, the administration might be the result of environmental and/or nutritional exposure of test agents.

EXAMPLES

Example 1: Cell Culture and Lysis for Mass Spectrometric Experiments

Cells were cultured in DMEM medium or RPMI 1640 medium supplemented with 10% fetal bovine serum and penicillin/streptomycin. Cells were harvested at about 80% confluency. After complete aspiration of medium from the plates, cells were scraped off the plate in 10 ml lysis buffer per $2 \times 10^8$ cells (20 mM HEPES pH 8.0, 9 M urea, 1 mM sodium vanadate, supplemented with 2.5 mM sodium pyrophosphate, 1 mM β-glycerol-phosphate) and sonicated. Sonicated cell lysates were cleared by centrifugation at 20,000×g.

Example 2: Protein Digestion

Lysate proteins were reduced with DTT at a final concentration of 4.1 mM and alkylated with iodoacetamide at 8.3 mM. For digestion, protein extracts were diluted in 20 mM HEPES pH 8.0 to a final concentration of 2 M urea and endoproteinase GluC (Worthington, 1 mg/ml in 20 mM Hepes pH 8.0) was added at 1/100 of the digestion volume. Digestion was performed overnight at room temperature.

Example 3: Reversed-Phase Solid-Phase Extraction of Digests

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2\times10^8$ cells. Columns were washed with 15 volumes of 0.1% TFA. A peptide fraction was obtained by elution with 3×2 volumes of 40% MeCN in 0.1% TFA. Peptide were lyophilized.

Example 4: Immunoaffinity Purification (IAP) of Peptides

Peptides (0.8 to 5 mg per cell sample) were dissolved in 1.4 ml of IAP buffer (50 mM MOPS pH 7.2, 10 mM sodium phosphate, 50 mM NaCl), briefly sonicated in a water bath, and insoluble matter was removed by centrifugation. The peptide solution was added to mutation-specific antibody or mixtures of mutation-specific antibodies, with each antibody coupled at 5 ug to a total volume of 40 ul beads of protein A agarose (Roche). The antibody/peptide mixture was incubated overnight at 4° C. with gentle shaking. The immobilized antibody beads were washed three times with 1 ml IAP buffer and twice with 1 ml water, all at 0-4° C. Peptides were eluted from beads by incubation with 55 μl of 0.15% TFA at room temperature for 10 min (eluate 1), followed by a wash of the beads (eluate 2) with 45 μl of 0.15% TFA. Both eluates were combined. The IAP eluate was purified by 0.2 μl C18 microtips (StageTips). Peptides were eluted from the microcolumns with 4 μl of 60% MeCN, 0.1% TFA and dried in a SpeedVac. After drying, the peptide was redissolved in 5 ul of 5% MeCN, 0.1% TFA.

Example 5: Analysis by LC-MS 4 ul of redissolved peptide was loaded onto a 10 cm×75 μm PicoFrit capillary column (New Objective) packed with Magic C18 AQ reversed-phase-resin (Michrom Bioresources) using a Famos autosampler with an inert sample injection valve (Dionex). The column was then developed with a 45-min linear gradient of acetonitrile delivered at 200 nl/min (Ultimate, Dionex), and MS spectra were collected with an Orbitrap mass spectrometer. MS1 peaks were analyzed against theoretical masses using MZmine software, see Katajamaa et al., Bioinformatics. 2006 January; 22(5): 634-6.

Example 6

Diverse cell lines each carrying one of three mutations to be detected with the methods described herein were harvested, and proteins were digested with the endoproteinase GluC. After purification by C18 chromatography, cellular peptides were subjected to immunoaffinity purification (LAP) with appropriate antibodies in order to enrich for peptides carrying the mutation screened for, and subsequent mass spectrometric analysis. Peptide IAPs were performed on 5 mg of peptide.

Example 7

The mutation L858R in the EGF receptor was detected in H3255 cells after IAP enrichment of peptide with an antibody recognizing the mutated peptide sequence (i.e., the mutant signature peptide). The lack of detection of the mutated peptide sequence in H1650 and HCC827 cells, which both do not carry this mutation, served as negative control.

Example 8

The mutation resulting in the E746-A750 deletion in the EGF receptor was detected in H1650 and HCC 827 cells after IAP enrichment of peptide with an antibody recognizing the mutated peptide sequence. The lack of detection of the mutated peptide sequence in H3255 and H1975 cells, which both do not carry this mutation, served as negative control.

Example 9

The mutation G12S in the small G protein K-Ras, as well as wild-type K-Ras, was detected in A549 cells after IAP enrichment of peptide with an antibody recognizing the peptide sequence stretching across the mutated amino acid.

Example 10

Peptides from three cell lines carrying three different mutations were mixed and mutated peptides were captured with a mixture three antibodies. Peptides from H3255 cells (for EGFR L858R mutation), H 1650 cells (for EGFR del 746-750 mutation), and A 549 cells (for K-Ras G12S mutation) were mixed in equal amounts, at 0.8 mg peptide of each cell lysate. The peptide mix was subjected to IAP with a mix of the three mutation antibodies. All three mutations were detected by MS1 with good intensity. The chromatographic retention time of the peptides perfectly aligned with the retention time of synthetic heavy-isotope peptides of the same amino acid sequence (i.e., standard peptides), further confirming identity, beyond the accurate mass readout. Intensities of mutated peptides were in the range of 6E5 to 8E6, while the current detection limit of the mass spectrometer is in the low E4 range. This will allow for significant reduction in the sample amount needed for detection.

Figure 1:
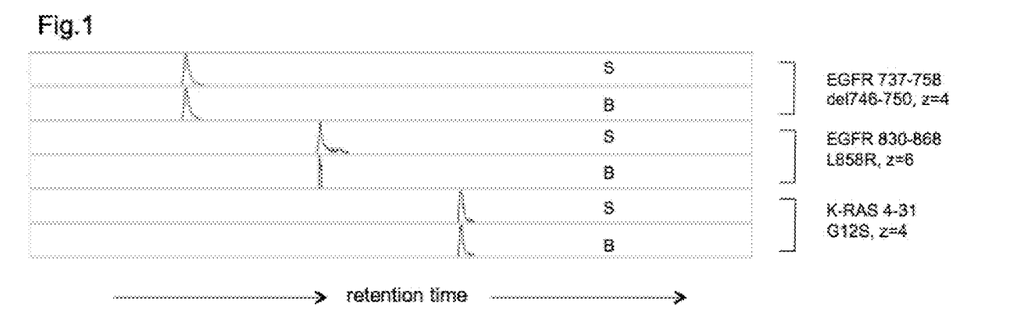
FIG. 1. Coelution of synthetic heavy isotope peptides and biological peptides in Example 10. S=synthetic peptide, B=biological peptide.
Figure 2:
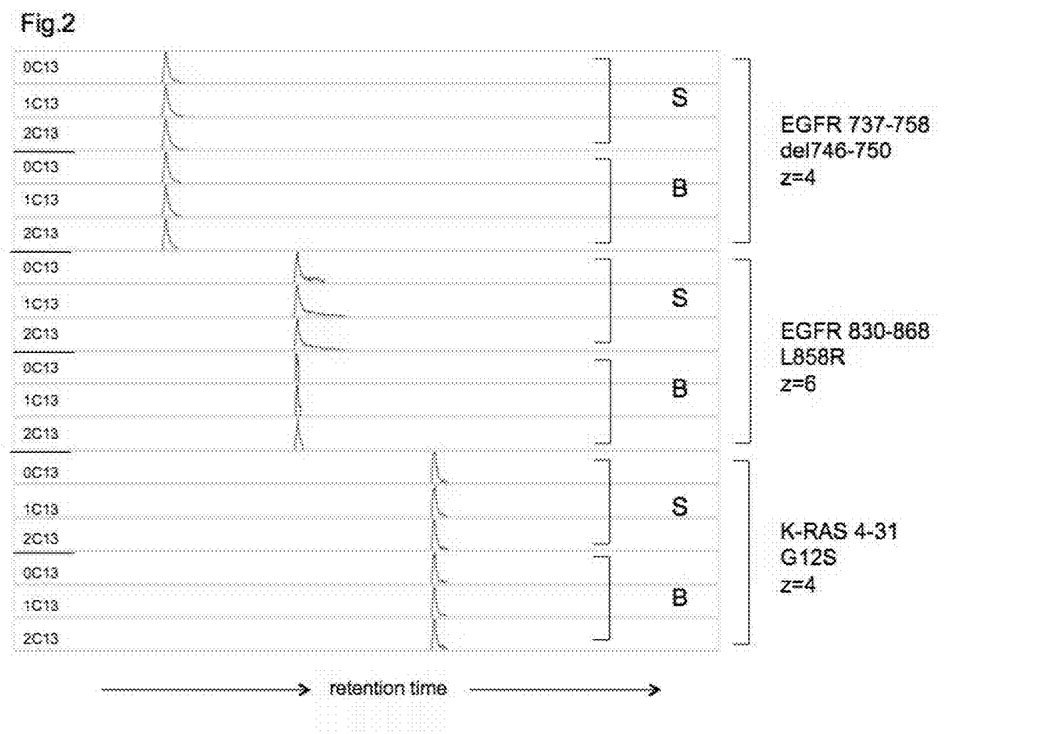
FIG. 2. As FIG. 1, but shows also coelution of 1C13 and 2C13 peptides (peptide isotopes containing 1 and 2 C13 atoms, respectively).

FIG. 1 shows the co-elution of synthetic heavy isotope peptides and biological peptides as described in this example. FIG. 2 shows the co-elution of synthetic heavy isotope peptides and biological peptides with the coelution of 1C13 and 2C13 peptides (peptide isotopes containing 1 and 2 C13 atoms, respectively). This coelution of peptide isotopes confirms the status of the peaks as peptides as opposed to noise (important for lower intensities than observed in this experiment), and shows agreement of observed charge state of the peptide with the theoretically expected one (if peptides were of a different charge state, the m/z values of the isotopes would show a different spacing from one another). The calculated and measured m/z values of the peptides show in FIG. 2 are set forth below in Table 1.

TABLE 1

| Peptide | Labeling | Calculated m/z | Measured m/z |
| --- | --- | --- | --- |
| EGFR 737-758 del746-750, synth. heavy isotope peptide | 0C13 | 465.04456 | 465.04443 |
| | 1C13 | 465.29528 | 465.29492 |
| | 2C13 | 465.54597 | 465.54558 |
| EGFR 737-758 del746-750, biological peptide | 0C13 | 463.54111 | 463.54103 |
| | 1C13 | 463.79183 | 463.79175 |
| | 2C13 | 464.04252 | 464.04245 |
| EGFR 830-868 L858R, synth. heavy isotope peptide | 0C13 | 748.59511 | 748.59552 |
| | 1C13 | 748.76225 | 748.76257 |
| | 2C13 | 748.92937 | 748.92957 |
| EGFR 830-868 L858R, biological peptide | 0C13 | 747.42559 | 747.42609 |
| | 1C13 | 747.59272 | 747.59302 |
| | 2C13 | 747.75984 | 747.76007 |
| K-Ras 4-31 G12S, synth. heavy isotope peptide | 0C13 | 748.66911 | 748.66956 |
| | 1C13 | 748.91983 | 748.92010 |
| | 2C13 | 749.17054 | 749.17078 |

TABLE 1-continued

| Peptide | Labeling | Calculated m/z | Measured m/z |
|---|---|---|---|
| K-Ras 4-31 G12S, biological peptide | 0C13 | 747.16565 | 747.16608 |
|  | 1C13 | 747.41638 | 747.41681 |
|  | 2C13 | 747.66708 | 747.66748 |

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited above are incorporated herein by reference in their entirety to the extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A method for determining the presence of at least one distinct polypeptide in a biological sample, wherein the at least one distinct polypeptide contains a mutation or post-translational modification relative to a wild type or unmodified polypeptide, respectively, the method comprising:
   (a) contacting the biological sample with a hydrolyzing agent, wherein the hydrolyzing agent is capable of hydrolyzing the distinct polypeptide in a sequence-specific manner such that at least one distinct peptide comprising said mutation or post-translational modification and having a predetermined peptide measured accurate mass would result if the at least one distinct polypeptide were present in the biological sample, to obtain a hydrolyzed sample;
   (b) bringing the hydrolyzed sample in contact with a substrate comprising at least one immobilized binding partner, wherein the at least one immobilized binding partner is capable of specifically binding the distinct peptide;
   (c) removing the hydrolyzed sample from the substrate in a manner such that the distinct peptide would remain bound to the immobilized binding partner;
   (d) contacting the substrate with an elution solution, wherein the distinct peptide would dissociate from the immobilized binding partner into the elution solution, to obtain an elution solution comprising a plurality of molecules;
   (e) determining the measured accurate mass of at least one molecule present in the elution solution; and
   (f) determining the presence of the at least one distinct polypeptide in the biological sample when a measured accurate mass of at least one molecule is substantially equal to the predetermined peptide measured accurate mass of the at least one distinct peptide.

2. The method of claim 1, wherein at least one standard peptide is added to the plurality of molecules, wherein the at least one standard peptide has substantially the same amino acid sequence as the at least one distinct peptide but a different measured accurate mass.

3. The method of claim 1, wherein at least two reference peptides are added to the plurality of molecules, wherein the at least two reference peptides have a known liquid chromatography elution order.

4. The method of claim 2, wherein the standard peptide comprises an isotope selected from the group consisting of $^{15}N$, $^{13}C$, $^{18}O$ and $^{2}H$.

5. The method of claim 2, wherein the at least one standard peptide and the at least one distinct peptide co-segregate during liquid chromatography.

6. The method of claim 4, wherein the presence of the at least one distinct polypeptide is confirmed by the co-segregation of the at least one standard peptide and the at least one molecule and by the difference in measured accurate mass between the at least one standard peptide and the at least one molecule.

7. The method of claim 1, wherein the plurality of molecules are segregated during liquid chromatography according to a feature selected from the group consisting of hydrophobicity, charge, and retention time.

8. The method of claim 2, wherein the at least one standard peptide and the at least one distinct peptide have a substantially identical retention time.

9. The method of claim 1, wherein the mutation is an addition, deletion and/or substitution of about 1 to about 10 amino acid residues.

10. The method of claim 1, wherein the post-translational modification is selected from the group consisting of phosphorylation, acetylation, ubiquitination, and glycosylation.

11. The method of claim 1, wherein the biological sample is derived from saliva, mucous, tears, blood, serum, lymph fluids, buccal cells, circulating tumor cells, mucosal cells, biopsy tissue, cerebrospinal fluid, semen, feces, plasma, urine, a suspension of cells, or a suspension of cells and viruses.

12. The method of claim 1, wherein the biological sample comprises a number of different polypeptides selected from the group consisting of between about 5,000 to about 20,000 different polypeptides, between about 7,500 to about 15,000 different polypeptides, and up to about 100,000 different polypeptides and isoforms thereof.

13. The method of claim 1, wherein the hydrolyzing agent is selected from the group consisting of an enzyme and a chemical.

14. The method of claim 1, wherein the hydrolyzing agent is selected from the group consisting of cyanogen bromide, BNPS-Skatole, formic acid, trypsin, Lysine-C endopeptidase (LysC); arginine-C endopeptidase (ArgC), Asp-N, glutamic acid, endopeptidase (GluC), chymotrypsin, and combinations thereof.

15. The method of claim 1, wherein the substrate comprises a substance selected from the group consisting of a gel matrix and polymer beads.

16. The method of claim 1, wherein the at least one immobilized binding partner comprises a reagent selected from the group consisting of an antibody or peptide binding fragment thereof, a protein that specifically binds to the distinct peptide, an antibody or antibody fragment that binds a mutant signature peptide, and an antibody or antibody fragment that binds a wild type peptide.

17. The method of claim 1, wherein the at least one immobilized binding partner is 1 to about 500 or 1 to at least 500 immobilized binding partners, wherein each immobilized binding partner specifically binds to a different distinct peptide.

18. The method of claim 1, wherein the determining measured accurate mass includes the step of ionization of the at least one molecule by a method selected from the group consisting of Atmospheric Pressure Chemical Ionization (APCI), Chemical Ionization (CI), Electron Impact (EI), Electrospray Ionization (ESI), Fast Atom Bombardment (FAB), Field Desorption/Field Ionization (FD/FI), Matrix Assisted Laser Desorption Ionization (MALDI), and Thermospray Ionization.

19. The method of claim 1, wherein determining the measured accurate mass is performed using an instrument selected from the group consisting of an instrument with a mass accuracy of 5 ppm or less and an instrument with a mass accuracy of 1 ppm or less.

20. The method of claim 1, wherein the biological sample is depleted of a protein selected from the group consisting of albumin, IgG, IgA, transferrin, haptoglobin, and antitrypsin; or combinations thereof, prior to step (a).

* * * * *